United States Patent
Bowen et al.

(10) Patent No.: US 10,894,157 B2
(45) Date of Patent: Jan. 19, 2021

(54) LASER MARKING OF RAW ANODE FOIL TO INDUCE UNIFORM PATTERING AND ETCHING WITH OXIDE PASSIVATION MASK

(71) Applicant: Pacesetter, Inc., Santa Clara, CA (US)

(72) Inventors: David R. Bowen, Taylors, SC (US); Ralph Jason Hemphill, Sunset, SC (US); Kurt J. Erickson, Anderson, SC (US)

(73) Assignee: Pacesetter, Inc., Santa Clara, CA (US)

(*) Notice: Subject to any disclaimer, the term of this patent is extended or adjusted under 35 U.S.C. 154(b) by 192 days.

(21) Appl. No.: 15/933,158

(22) Filed: Mar. 22, 2018

(65) Prior Publication Data
US 2018/0280689 A1 Oct. 4, 2018

Related U.S. Application Data

(60) Provisional application No. 62/481,433, filed on Apr. 4, 2017.

(51) Int. Cl.
| | |
|---|---|
| *B23K 26/00* | (2014.01) |
| *A61N 1/05* | (2006.01) |
| *B23K 26/082* | (2014.01) |
| *B23K 26/073* | (2006.01) |
| *H01G 9/045* | (2006.01) |
| *B23K 26/0622* | (2014.01) |
| *H01G 9/00* | (2006.01) |
| *H01G 9/055* | (2006.01) |
| *B23K 26/362* | (2014.01) |
| *B23K 26/359* | (2014.01) |

(Continued)

(52) U.S. Cl.
CPC ........ *A61N 1/0563* (2013.01); *B23K 26/0624* (2015.10); *B23K 26/073* (2013.01); *B23K 26/082* (2015.10); *B23K 26/359* (2015.10); *B23K 26/361* (2015.10); *B23K 26/362* (2013.01); *H01G 9/0029* (2013.01); *H01G 9/0032* (2013.01); *H01G 9/045* (2013.01); *H01G 9/055* (2013.01); *A61N 1/3956* (2013.01); *A61N 1/3975* (2013.01)

(58) Field of Classification Search
None
See application file for complete search history.

(56) References Cited

U.S. PATENT DOCUMENTS

| | | |
|---|---|---|
| 3,779,877 A | 12/1973 | Alwitt |
| 4,474,657 A | 10/1984 | Arora |
| 4,518,471 A | 5/1985 | Arora |

(Continued)

*Primary Examiner* — Shamim Ahmed (57) ABSTRACT

A method of producing an electrode for use in the manufacture of electrolytic capacitors for implantable cardioverter defibrillators comprises first growing a hydrate layer and/or formed oxide layers of the foil, applying a laser beam to portions of the foil to ablate the aluminum oxide foil surface before etching in order to induce etching in the specific areas, and then, etching the foil. The laser marks the oxide layer in a pulsed spot pattern through the hydrate layer and/or formed oxide layer leaving a dimpled nascent aluminum surface. The oxide layer left behind is a mask and the fresh aluminum areas are the high etching activation sites. After marking the aluminum oxide foil surface, the foil may be electrochemically etched in an electrolyte containing chloride and/or various oxidative species.

21 Claims, 10 Drawing Sheets

(51) Int. Cl.
*B23K 26/361* (2014.01)
*A61N 1/39* (2006.01)

(56) References Cited

U.S. PATENT DOCUMENTS

| | | | |
|---|---|---|---|
| 4,525,249 | A | 6/1985 | Arora |
| 5,522,851 | A | 6/1996 | Fayram |
| 5,715,133 | A | 2/1998 | Harrington et al. |
| 7,130,183 | B1 | 10/2006 | Fayram |
| 7,175,676 | B1 * | 2/2007 | Stevens ............... H01G 9/0032 29/25.03 |
| 7,196,899 | B1 | 3/2007 | Feger et al. |
| 7,452,473 | B1 | 11/2008 | Hemphill et al. |
| 7,578,924 | B1 * | 8/2009 | Jiang ....................... C25F 3/04 205/640 |
| 8,734,964 | B2 | 5/2014 | Kurihara et al. |
| 9,852,849 | B2 | 12/2017 | Hemphill et al. |
| 2004/0182717 | A1 * | 9/2004 | Kinard ..................... C25D 5/18 205/233 |
| 2006/0076243 | A1 * | 4/2006 | Aoyama ................... C25D 5/44 205/153 |
| 2015/0179348 | A1 * | 6/2015 | Ribble ................. H01G 9/055 428/209 |
| 2015/0225890 | A1 * | 8/2015 | Canonico ............... D06M 11/83 428/196 |
| 2017/0207030 | A1 * | 7/2017 | Strange ................. H01G 9/042 |
| 2017/0326686 | A1 | 11/2017 | Hemphill et al. |

\* cited by examiner

LASER MARKING OF RAW ANODE FOIL TO INDUCE UNIFORM PATTERING AND ETCHING WITH OXIDE PASSIVATION MASK

PRIORITY

The present application relates to and claims priority from U.S. provisional patent application Ser. No. 62/481,433, filed Apr. 4, 2017, entitled "LASER MARKING OF RAW ANODE FOIL TO INDUCE UNIFORM PATTERING AND ETCHING WITH OXIDE PASSIVATION MASK," which is hereby expressly incorporated by reference in their entirety to provide continuity of disclosure.

BACKGROUND OF THE INVENTION

Field of the Invention

The present invention is directed to a method of producing an electrode for use in the manufacture of electrolytic capacitors and more particularly to a method of creating porous electrode foil for use in multiple electrode stack configuration electrolytic capacitors of the type used in implantable cardioverter defibrillators (ICDs).

Related Art

Compact, high voltage capacitors are utilized as energy storage reservoirs in many applications, including implantable medical devices. These capacitors are required to have a high energy density since it is desirable to minimize the overall size of the implanted device. This is particularly true of an implantable cardioverter defibrillator (ICD), also referred to as an implantable defibrillator, since the high voltage capacitors used to deliver the defibrillation pulse can occupy as much as one third of the ICD volume.

Electrolytic capacitors are used in ICDs because they have the most near ideal properties in terms of size and ability to withstand relatively high voltage. Conventionally, an electrolytic capacitor includes an etched aluminum foil anode, an aluminum foil or film cathode, and an interposed kraft paper or fabric gauze separator impregnated with a solvent-based liquid electrolyte. The electrolyte impregnated in the separator functions as the cathode in continuity with the cathode foil, while an oxide layer on the anode foil functions as the dielectric. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, composing a planar, layered, stack structure of electrode materials with separators interposed therebetween.

Since these capacitors must typically store approximately 30-40 joules, their size can be relatively large, and it is difficult to package them in a small implantable device. A patient who has a device implanted may often be bothered by the presence of the large object in his or her pectoral region. Furthermore, the generally rectangular shape can in some instances lead to pocket erosion at the somewhat curved corners of the device. For the comfort of the patient, it is desirable to make smaller and more rounded ICDs. The size and configuration of the capacitors has been a major stumbling block in achieving this goal.

In ICDs, as in other applications where space is a critical design element, it is desirable to use capacitors with the greatest possible capacitance per unit volume. Since the capacitance of an electrolytic capacitor increases with the surface area of its electrodes, increasing the surface area of the aluminum anode foil results in increased capacitance per unit volume of the electrolytic capacitor. By electrolytically etching aluminum foils, an enlargement of a surface area of the foil will occur. As a result of this enlargement of the surface area, electrolytic capacitors, which are manufactured with the etched foils, can obtain a given capacity with a smaller volume than an electrolytic capacitor.

In a conventional electrolytic etching process, surface area of the foil is increased by electrochemically removing portions of the foil to create etch dimples. For example, U.S. Pat. Nos. 4,474,657, 4,518,471 and 4,525,249 to Arora, each of which is incorporated herein by reference, disclose the etching of aluminum electrolytic capacitor foil by passing the foil through an electrolyte bath. The preferred bath contains 3% hydrochloric acid and 1% aluminum as aluminum chloride. The etching is carried out under a direct current (DC) and at a temperature of 75° C. U.S. Pat. No. 4,474,657 is limited to the above single step. U.S. Pat. No. 4,518,471 adds a second step where the etched foil is treated in a similar bath with a lower current density and at a temperature of 80-82.5° C. U.S. Pat. No. 4,525,249 adds a different second step, where the etched foil is treated in a bath of 8% nitric acid and 2.6% aluminum as a nitrate, at a temperature of 85° C.

U.S. Pat. No. 7,452,473, incorporated herein by reference, discloses a method of producing an electrode for a capacitor from a foil. The method comprises, first, applying a laser beam to portions of the foil to create a pattern on the foil and, second, etching the foil. Patterns formed include patterns such as horizontal or vertical lines, a grid pattern, a crossed-grid pattern, a parallel wave pattern, an intersecting wave pattern, a labyrinth pattern, a staggered hole pattern, or alternatively an irregular pattern.

U.S. Pat. No. 8,734,964 to Kurihara, incorporated herein by reference, discloses laminating an etching resist over a molded material or sequentially laminating a first heat-generating layer, a second heat-generating layer, and a metal compound layer including a metallic oxynitride layer containing a metallic oxynitride over a molded material. The first heat-generating layer, the metallic oxynitride layer, and the second heat-generating layer are directly or indirectly laminated such that the metallic oxynitride layer is positioned between the first heat-generating layer and the second heat-generating layer. A laser beam is irradiated over the laminated etching resist to form penetrating holes in the etching resist.

There remains a need for an improved method for etching anode foil.

SUMMARY OF THE INVENTION

The present invention is directed to a method of producing an electrode for a capacitor from a foil. The method comprises, first, growing a hydrate layer and/or formed oxide layers of the foil, applying a laser beam to portions of the foil to ablate the aluminum oxide foil surface before etching in order to induce etching in the specific areas, and then, etching the foil. In certain embodiments, the laser marks the oxide layer in a pulsed spot pattern through the hydrate layer and/or formed oxide layer leaving a dimpled nascent aluminum surface. The oxide layer left behind is a mask and the fresh aluminum areas are the high etching activation sites. After marking the aluminum oxide foil surface, the foil may be electrochemically etched in an electrolyte containing chloride and/or various oxidative species. By appropriately spacing the laser spots in a close packed, e.g., hexagonal array, the foil capacitance can be maximized by causing pattern etching of the foil surface. In certain embodiments, the laser pulse is delivered in the femtosecond time frame in order to increase the speed of marking and to provide an advantageously high ratio of peak to average power which maximizes ablation efficiency of the protective oxide layer while essentially eliminating thermally induced damage of the desirably engineered cubic structure of the underlying aluminum substrate. In certain embodiments, a 'femtosecond class' laser is used.

It is to be understood that both the foregoing general description and the following detailed description are exemplary and explanatory and are intended to provide further explanation of the invention as claimed.

BRIEF DESCRIPTION OF THE DRAWINGS/FIGURES

The accompanying drawings, which are included to illustrate exemplary embodiments of the invention and are incorporated in and constitute a part of this specification, illustrate embodiments of the invention and together with the description serve to explain the principles of the invention. In the drawings.

DETAILED DESCRIPTION OF THE INVENTION

In the detailed description that follows, references to "one embodiment," "an embodiment," "an illustrative embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

It should be understood that not all embodiments of the invention include the discussed features, advantages or modes of operation. Alternate embodiments may be devised without departing from the scope of the invention, and well-known elements of the invention may not be described in detail or may be omitted so as not to obscure the relevant details of the invention. In addition, the terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises," "comprising," "includes" "including" and/or "having," when used herein, specify the presence of stated features, steps, operations, elements, and/or components, but do not preclude the presence or addition of one or more other features, steps, operations, elements, components, and/or groups thereof.

In accordance with the present disclosure, improved anode foils and methods of fabricating these improved structures are provided. Various advantages and benefits accrue for the embodiments disclosed herein. An elaboration of some of these advantages and benefits is provided below. It is noted that the following list of advantages and benefits is for purposes of illustration and not limitation.

The techniques, materials and methods disclosed herein may be used, for example, to manufacture anodes, anode stacks and capacitors containing such anodes and anode stacks, such as those disclosed in U.S. Pat. No. 7,130,183 to Fayram and/or U.S. Pat. No. 7,196,899 to Feger et al., both of which are incorporated herein by reference as if reproduced in full below.

The method comprises growing a hydrate layer and/or formed oxide layers on a metal foil surface and using a laser to ablate the metal foil surface before etching in order to induce etching in specific areas. By appropriately spacing the laser spots in a close packed array, the foil capacitance can be maximized by causing pattern etching of the foil surface that increase the surface area of the metal foil. The foil can be used as anodes, which in turn are used in assembling a capacitor. The increased surface area for the anodes may equate to a reduction in overall capacitor volume of about 50-66%, which in terms of current ICD volume is a 9 to 12 cc reduction. Or alternatively, fewer anodes may be needed to deliver the same energy output, thereby reducing production costs of the capacitor.

Growing Hydrate Layer

Figure 1A:
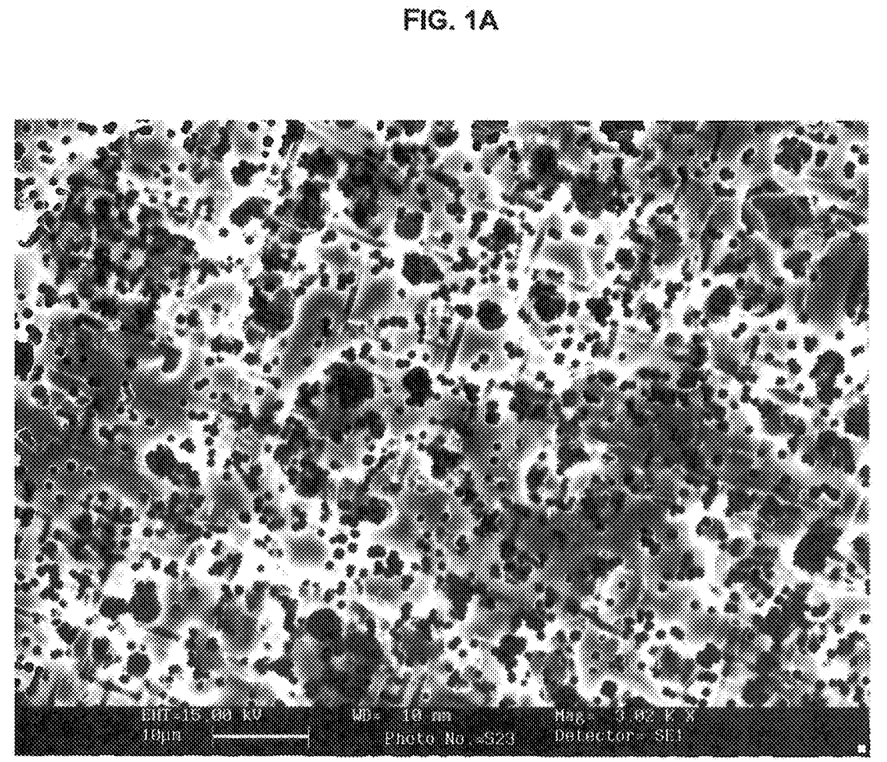
FIG. 1A is a Scanning Electron Microscope (SEM) photograph of an aluminum foil electrochemically etched and widened using conventional methods.
Figure 1B:
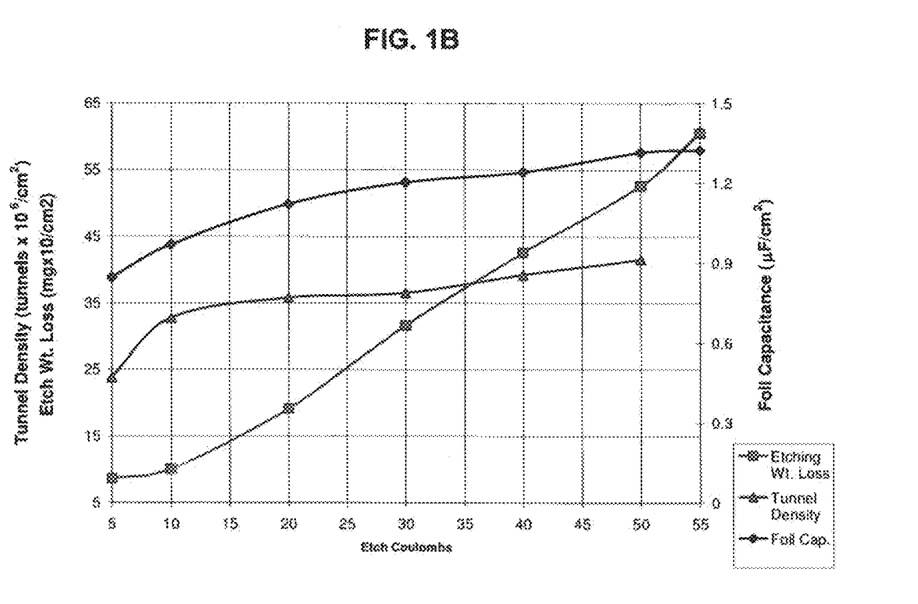
FIG. 1B is shows a graph highlighting the effects of conventional etching processes on foil properties.
Figure 1C:
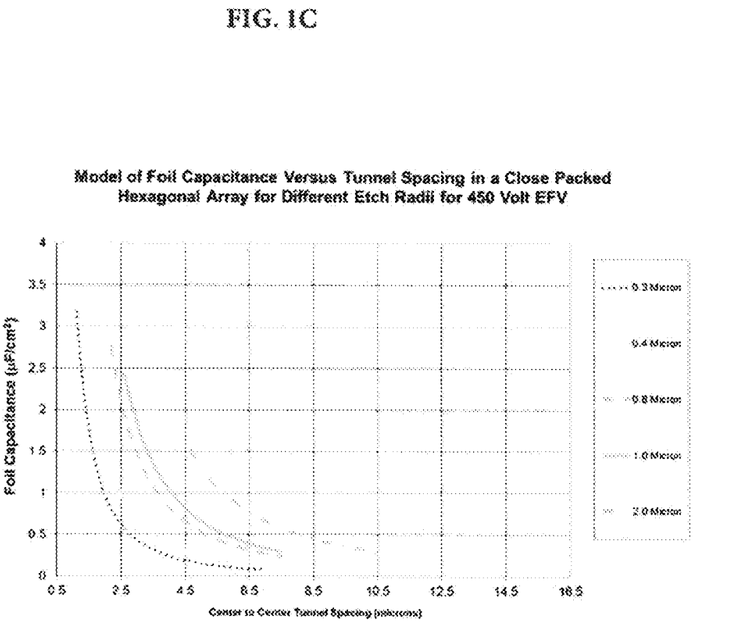
FIG. 1C shows results measuring capacitance verses dimple spacing in a close-packed hexagonal array for different etching radii for a 450 Volt EFV (effective formation voltage) foils.
Figure 2A:
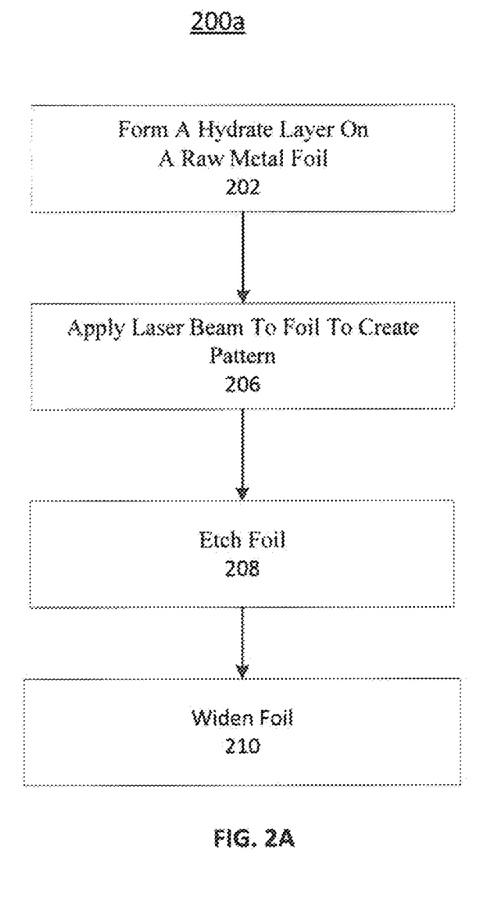
FIGS. 2A-2C are flow diagrams showing methods of producing an electrode with, first, growing a hydrate layer and/or formed oxide layers of the foil, and applying a laser beam to portions of the foil to ablate the aluminum oxide foil surface before etching in order to induce etching in specific areas.

FIG. 2A is a high level flowchart of an exemplary method 200a of imparting a pattern on a metal foil surface. The method 200a can include step 202 of forming a hydrate layer on a raw metal foil. In certain embodiments, the metal foil is aluminum foil. In certain embodiments, the metal foil is tantalum foil. In some embodiments, a hydrate layer can be created by dipping the surface of metal substrate in a bath of water. Water reacts with the exposed areas of metal substrate to form a hydrate layer above and below the surface of metal substrate. The hydrate layer thus forms a mask above and below the surface of metal substrate thereby forming a layer of protection that extends below the surface of a metal substrate.

The following is an exemplary process for creating a hydrate layer when an aluminum foil is used as the metal substrate. The aluminum foil can be dipped in 95° C. deionized (DI) water for 4 to 12 minutes, preferably 8 minutes, to form aluminum hydroxide above and below the surface of the aluminum foil. In some embodiments, the temperature of the water is in a range from 70 to 100 degrees Celsius. The length of time to form the hydrate layer of a desired thickness is determined in part by the temperature as the higher the temperature, the shorter the length of time to form a hydrate layer, as would be appreciated by one of ordinary skill in the art. The hydrate layer may have a thickness of preferably from 7 to 200 nm, more preferably from 10 to 100 nm, and even more preferably from 15 to 70 nm.

Oxide Layer Formation

Figure 2B:
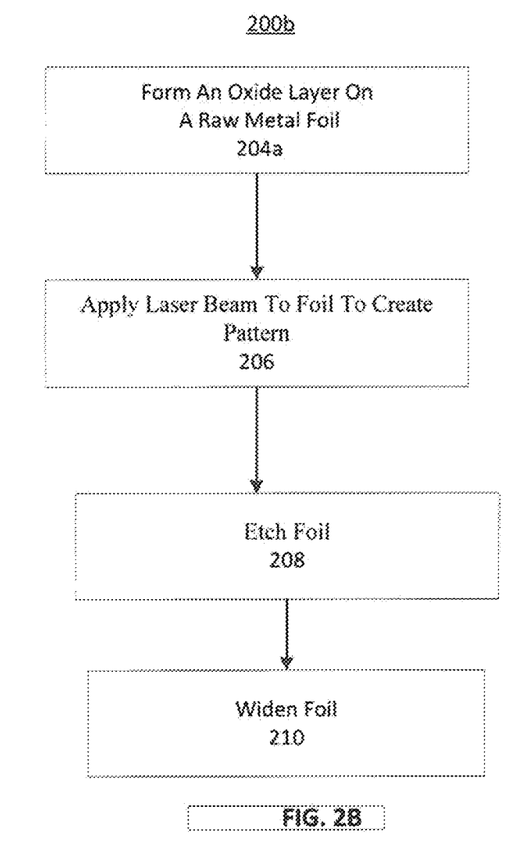

FIG. 2B is a high level flowchart of an alternative exemplary method 200b of imparting a pattern on a metal foil surface. The method 200b can include step 204a of forming an oxide layer on a raw metal foil. A barrier oxide layer may be electrochemically formed onto the surface of the metal foil by placing the foil into a forming solution, including but not restricted to a solution based on azelaic acid, sebacic acid, suberic acid, adipic acid, dodecanedioic acid, citric acid or other related organic acids and salts, preferably a citric acid solution at a temperature of 80° C. to 100° C., preferably 85° C., at a current density of 1 mA/cm$^2$ to 40 mA/cm$^2$, preferably 16 mA/cm$^2$. The oxide layer may have a thickness of preferably from 7 to 200 nm, more preferably from 10 to 100 nm, and even more preferably from 15 to 70 nm.

Forming Hydrate and Oxide Layers

Figure 2C:
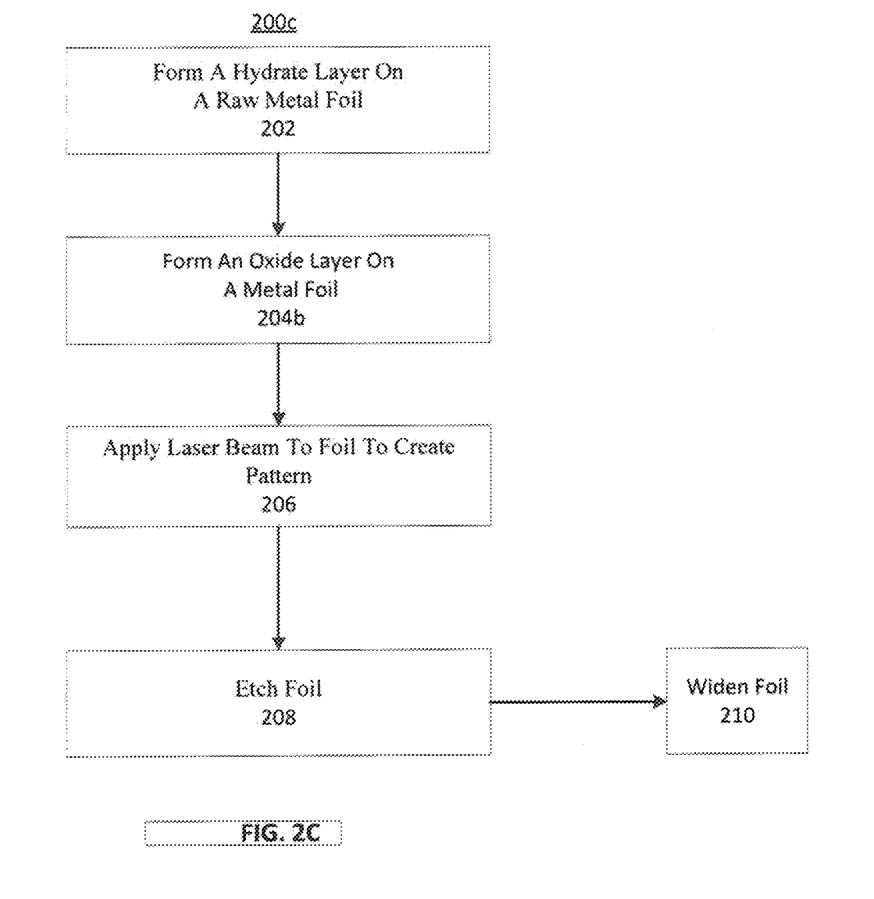

FIG. 2C is a high level flowchart of an alternative exemplary method 200c of imparting a pattern on a metal foil surface. The method 200c can include both step 202 of forming a hydrate layer on a raw metal foil and step 204b of forming an oxide layer onto surfaces of the metal foil.

Applying Laser Beam

At step 206 of method 200a (FIG. 2A), method 200b (FIG. 2B), and method 200c (FIG. 2C), a laser beam is applied to portions of the foil to ablate the metal foil, e.g., aluminum oxide foil, surface before etching in order to induce etching in specific areas. In certain embodiments, the laser marks the oxide layer in a pulsed spot pattern through the hydrate layer, leaving a dimpled nascent aluminum surface. The hydrate layer left behind is a mask and the fresh aluminum areas are the high etching activation sites. Advantageously, unlike a laminate layer disclosed in U.S. Pat. No. 8,734,964, which simply sits on the surface of the molded material, the hydrate layer of the current disclosure incorporates into the metal foil, e.g. the aluminum foil. Because the hydrate of the current disclosure incorporates into the metal foil, it does not peel off during etching, enhancing its effectiveness as a mask during the etching process.

The desired pulsed laser ablated spots are a diameter of about 1 to 10 microns with about 2 to 20 micron center to center spacing in a hexagonal close packed array. The depth of the laser mark should be through the hydrate layer to expose the fresh surface, e.g., aluminum foil, then 0.5 to 20 microns deep into the metal foil, without heating the substrate such that the cubic structure is damaged, or a protective thermal oxide is formed in the mark zone. In embodiments of the current disclosure, the laser does not penetrate through the substrate but instead merely provides dimples in the metal foil. Use of a laser pulse delivered in the femtosecond time frame is greatly preferred due to the speed of marking, and the phenomenally high ratio of peak to average power which maximizes ablation efficiency of the protective oxide layer while essentially eliminating thermally induced damage of the desirably engineered cubic structure of the underlying substrate, e.g., aluminum or tantalum substrate.

Example Laser Source

Figure 3A:
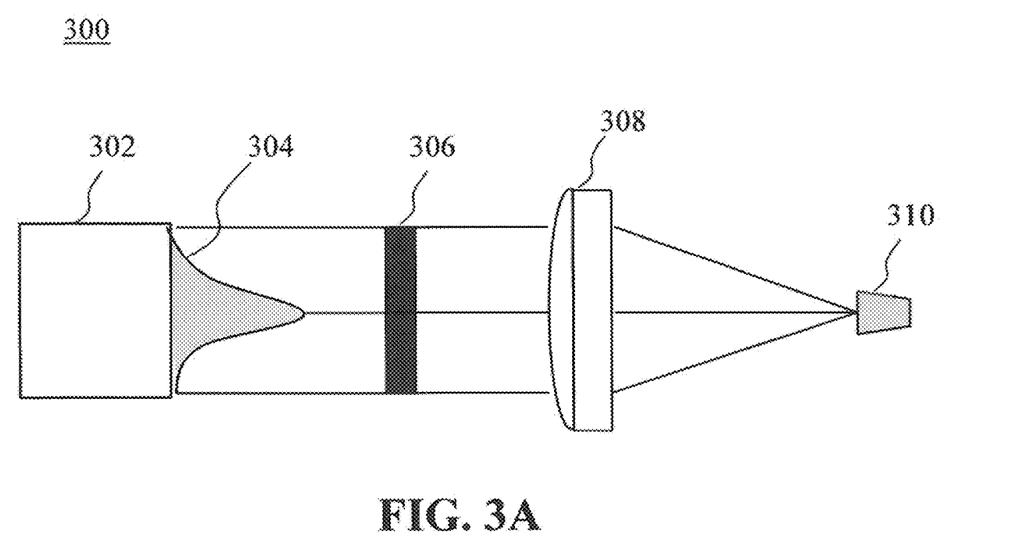
FIG. 3A illustrates an optical arrangement for generating a laser pulse, according to an embodiment.

FIG. 3A illustrates an optical arrangement 300 that includes a laser source 302, a beam shaping element 306, and a focusing element 308, according to an embodiment. Laser source 302 may include a pulsed laser having a wavelength between about 200 nm and 1070 nm. Laser source 302 may be designed as an ultrashort pulse source (i.e., having a picosecond or femtosecond pulse width). Use of a laser pulse delivered in the femtosecond time frame is preferred due to the speed of marking, and the phenomenally high ratio of peak to average power which maximizes ablation efficiency of the protective oxide layer while essentially eliminating thermally induced damage of the desirably engineered cubic structure of the underlying aluminum substrate.

In an embodiment, optical arrangement 300 is provided within a laser head that may be movable to ablate various portions of a sample. In another embodiment, only some components of optical arrangement 300 are provided within the laser head. For example, the laser head may only include focusing element 308.

Laser source 302 outputs a beam of light having a substantially Gaussian spatial profile 304. Although this beam of light may be used for ablation, it may be more difficult to control the ablation depth and/or volume of the beam spot given the energy distribution of Gaussian profile 304. This is discussed in more detail later with reference to FIG. 3B.

According to an embodiment, the beam of light with Gaussian profile 304 is received by a beam shaping element 306 and converted to a beam of light having a top hat spatial profile 310. For example, the beam of light with Gaussian profile 304 may have an M$^2$ value less than 1.2 while the beam of light having top hat profile 310 may have an M$^2$ value greater than 20. The M$^2$ value is a parameter that quantifies the beam quality of a laser beam. An ideal Gaussian beam has an M$^2$ value of 1, while higher M$^2$ values have a more uniform energy profile. Beam shaping element 306 may be a fused silica diffractive optic designed to modulate the energy profile of an input Gaussian beam. One example of beam shaping element 306 is the FBSR Beam Shaper from Topag Lasertechnik.

It should be understood that Gaussian profile 304 and top hat profile present a cross-sectional energy distribution of the laser beam at their respective locations along the optical path. The beam of light produced by laser source 302 may be characterized as having Gaussian profile 304 up until it is received by beam shaping element 306, after which the beam of light may be characterized as having top hat profile 310. In other embodiments, beam shaping element 306 is not included and the laser light characterized as having Gaussian profile 304 is focused by focusing element 308 onto a beam spot for ablation of a dimple through a metal foil.

The beam of light having the top hot profile 310 may then be focused onto a beam spot using focusing element 308. FIG. 3A illustrates how the focused beam of light has the top hat profile 310 due to beam shaping element 306. Focusing element 308 may represent one or more lenses arranged to focus the collimated light beam onto a beam spot for ablation of a dimple onto a metal foil, according to an embodiment.

Figure 3B:
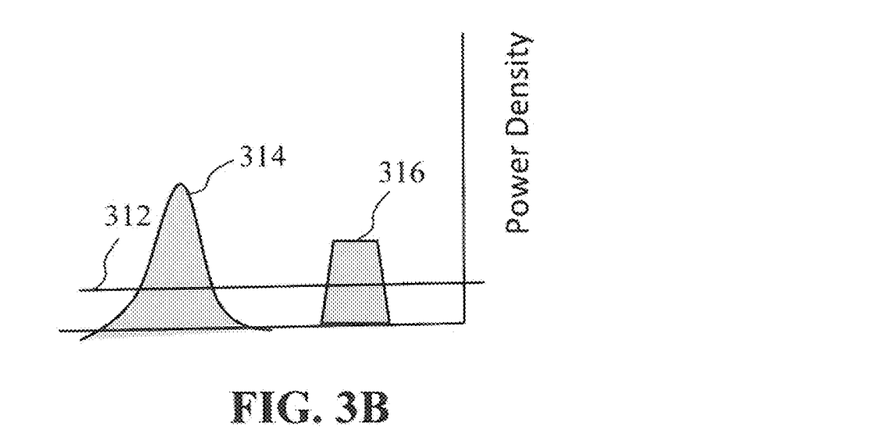
FIG. 3B illustrates a comparison between a Gaussian and a top-hat spatial profile.

FIG. 3B illustrates how the size of the resulting beam spot changes based on applied power density and energy profile of the beam. An ablation threshold 312 is indicated, which represents the power needed to start ablating through the hydrate/oxide layer and forming a dimple on the surface of the metal, without penetrating through the metal. As the beam spot is focused to include a narrower region of Gaussian profile 314, there is a high power output at the center of the beam spot and lower power output at the edges of the beam spot. Although ablation can occur using this energy profile, the resulting ablation morphology, e.g., depth and/or volume is more difficult to control, and the transfer of heat to the material is more significant, due to the substantial change in delivered power from the center of the beam spot to the edge of the beam spot.

At ablation threshold 312, top hot profile 316 provides a more uniform energy distribution across the beam spot, even as the beam spot is focused to include a narrower region of top hat profile 316. Thus, the ablation depth and/or volume is easier to control, has higher repeatability, and a better overall profile than with Gaussian profile 314.

Figure 3C:
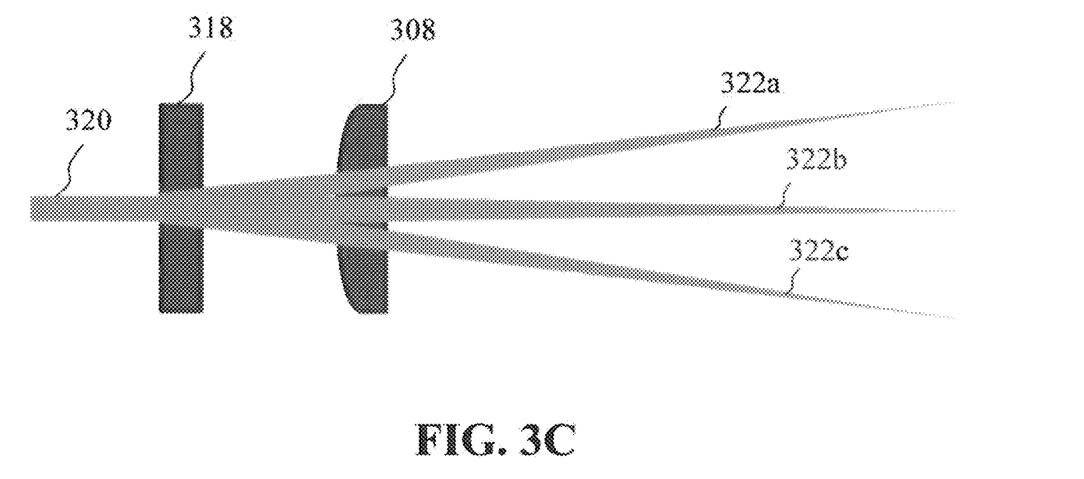
FIG. 3C illustrates a portion of the optical arrangement for generating multiple beam spots, according to an embodiment.

Only one output beam of light is illustrated in optical arrangement 300. However, in another embodiment, one or more optical elements may be included to split the beam of light having the top hat profile 310 into multiple beams of light that are each focused onto a metal foil at different beam spots. Beam splitting in this way may be achieved with diffractive optics to produce a linear or 2D array of beam spots having equal or nearly equal power densities. FIG. 3C illustrates an example of a diffractive splitting element 318, that may be used to split an incoming beam of light 320 into a plurality of light beams 322a-322c. Although only three light beams are illustrated here, it should be understood that any number of light beams may be generated. Diffractive splitting element 318 may be located optically downstream from shaping element 306 (if one is used), but optically upstream from focusing element 308.

Roller-Based Laser Drilling Technique

Figure 4A:
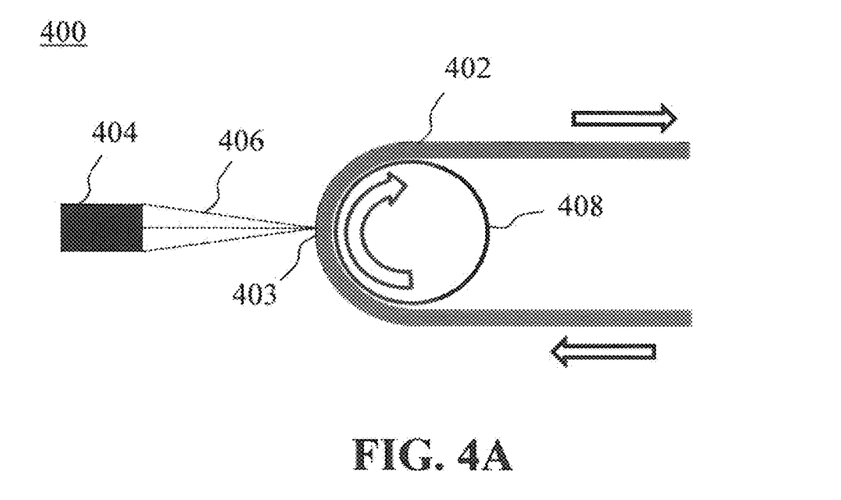
FIG. 4A illustrates a configuration for controlling laser ablation on a metal foil, according to an embodiment.

FIG. 4A illustrates a sheet roller arrangement 400 for ablating dimples on the surface of a metal foil 402, according to an embodiment. Metal foil 402 may be used as an anode in an electrolytic capacitor, and may be an aluminum or tantalum foil. A laser head 404 outputs a beam of light 406 having a top hat profile at a beam spot towards a surface of metal foil 402. The term "beam spot" as used herein refers to a location of focused light from the perspective of the laser head. Laser head 404 may have an internal arrangement similar to optical arrangement 300. In one embodiment, more than one beam of light having a top hat profile is outputted from laser head 404.

Metal foil 408 is stretched over a roller 408 such that a foil portion 403 faces laser head 404, according to an embodiment. Metal foil 402 may be stretched over roller 408 at any angle. Furthermore, metal foil 402 may be placed around other rollers or spooled around other rollers that are not shown for clarity. The arrows provide an example movement of metal foil 402 around roller 408. With respect to laser head 404, metal foil would appear to move upward. This direction is arbitrary, and it should be understood that other examples may have metal foil 402 moving downward with respect to laser head 404 and around roller 408 in a counter-clockwise direction. Laser head 404 may be designed to scan in a direction that is perpendicular to the direction that metal foil 402 moves around roller 408 (as viewed from laser head 404), such that beam of light 406 ablates dimples across a length of foil portion 403 (normal to the page in this illustration). This ablation method is illustrated in more detail in FIG. 4B.

Figure 4B:
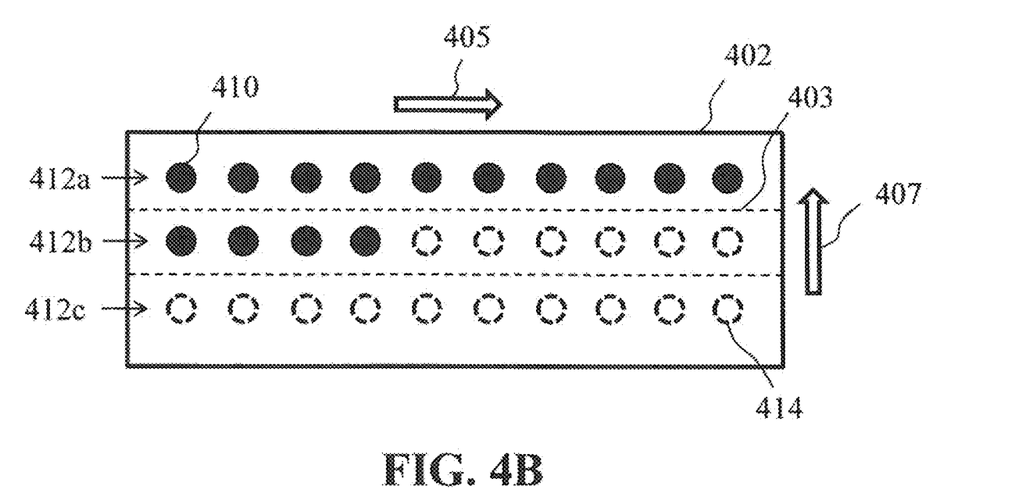
FIG. 4B illustrates an arrangement of dimples on a metal foil formed via the configuration of FIG. 3A, according to an embodiment.

FIG. 4B illustrates a view of metal foil 402 as viewed from laser head 404, according to an embodiment. Metal foil 402 includes a plurality of etched dimples 410 that are arranged in rows. Three example rows 412a-412c are illustrated in FIG. 4B, however, it should be understood that any number of rows of dimples may be ablated in metal foil 402. In the illustrated example, laser head 404 is scanned in a first direction 405 across a length of metal foil 402 and pulses energy towards metal foil 402 at a given beam spot to form a dimple 410. The laser power density being applied is above an ablation threshold of the metal foil. For example, the laser power density being applied may be between $7.8 \times 10^8$ W/cm$^2$ and $4 \times 10^{10}$ W/cm$^2$. In another example, the laser power density being applied is greater than $7.8 \times 10^8$ W/cm$^2$. In embodiments, the pulse repetition rate of the laser is approximately 50 MHz, and the scan head runs at the rate of 50 m/sec, such that the pits or dimples have a linear pitch of 1 micron per line. If the length of the scan line is 200 mm, the vertical scan rate is 500 lines/second. If the vertical pitch is 1 micron, then the web speed would be 500 microns/sec, or 30 mm/Min. In an embodiment, a pattern may be marked in 5.33 minutes per aluminum metal sheet of 320 cm$^2$ area.

Once a dimple has been formed, laser head 404 is laterally scanned in the first direction 405 and pulses energy towards metal foil 402 at a new beam spot to form the next dimple.

In the illustrated example, the entire first row 412a of dimples 410 have been ablated by beam of light 406. At this point, metal foil 402 may be moved in a second direction 407, such that the next row 412b is present as foil portion 403. The laser then proceeds to form dimples in row 412b.

The example illustrated in FIG. 4B shows that the laser has formed dimples partially along the length of row 412b, but has not yet formed dimples at locations 414 marked with broken circles. Additionally, the entire next row 412c includes all locations 414 where dimples have not yet been formed. Once each location 414 across row 412b has been ablated to form a dimple, metal foil 402 may again be moved in the second direction 407 to present row 412c as foil portion 403 to have its locations 414 ablated to form more dimples.

Figure 4C:
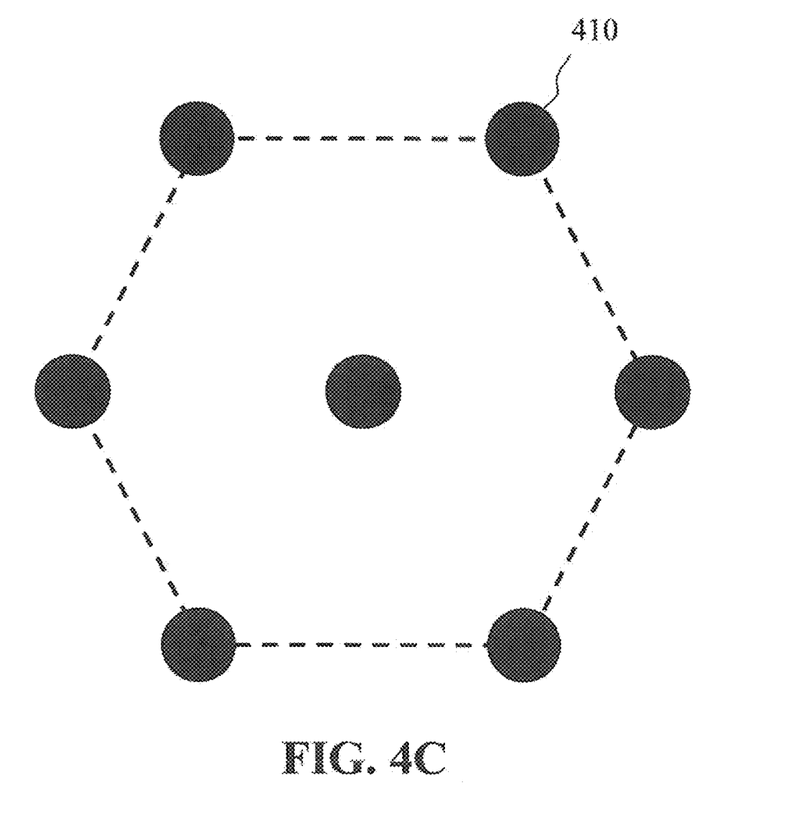
FIG. 4C illustrates a close packed hexagonal array arrangement of dimples, according to an embodiment.

It should be understood that many alterations may be made to how various elements move and when ablation takes place without deviating from the scope or sprit of the embodiments described herein. For example, laser head 404 may scan along the length of metal foil 402 in the first direction 405, forming dimples at each beam spot as it does, and then scan back across the length of metal foil 402 in the opposite direction to form dimples in the next row. In another example, roller 408 is laterally shifted in the first direction 405 while laser head 404 remains stationary. Laser head 404 may be controlled to form dimples 410 having any desired arrangement. For example, the packing density of dimples 410 may be a close packed hexagonal array arrangement, as illustrated in FIG. 4C. The overall dimple density may be on the order of 20 to 50 million dimples per $cm^2$. Furthermore, the diameters of the dimples may be changed by altering the beam spot size. Since the beam has a top-hat energy profile, changing the beam spot size would not adversely affect the ability for the laser beam to punch through a portion of the thickness of the foil and form the dimple. In certain embodiments, the dimple is 0.5 to 20 microns deep. In another example, larger diameter dimples may be formed by clustering beam spots close enough together that they overlap.

In an embodiment, multiple beam spots may be formed on the surface of metal foil 402 along a length of foil portion 403. In this way, multiple dimples may be ablated at substantially the same time. In the example illustrated, the first four dimples of row 412b may be ablated at the same time by projecting four beams of light and creating four beam spots linearly arranged in the first direction 405. Providing multiple beams would substantially decrease the time it takes to ablate dimples across the surface of metal foil 402.

Figure 5:
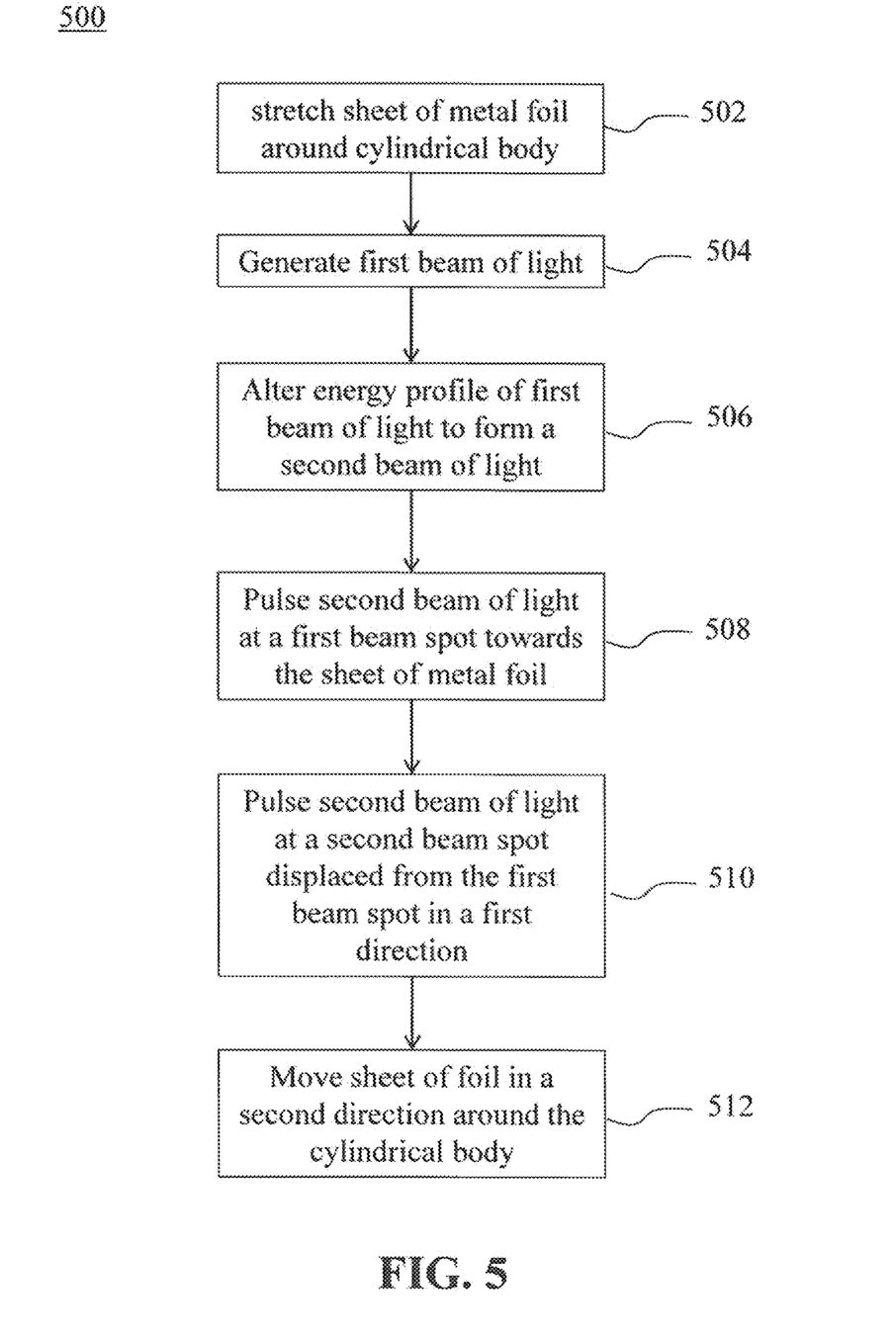
FIG. 5 illustrates a flow chart of a method of forming dimples on a metal foil, according to an embodiment.

FIG. 5 provides an example method 500 of ablating dimples in an anode foil. In one example, the anode foil is an aluminum foil or a tantalum foil that is used as the anode within a capacitor or battery. Any of the step(s) of method 500 may be performed using sheet roller arrangement 400. Furthermore, the various steps of method 500 may be performed in any order.

At block 502, a sheet of metal foil is stretched around a cylindrical body. The stretching may cause a portion of the foil to lay substantially flat across a length of the foil, where the portion is aligned with a laser head that delivers the pulses of light to ablate the foil.

At block 504, a first beam of light is generated. The first beam of light may be a beam of laser light having a wavelength between 200 nm and 1070 nm. The first beam of light may have a Gaussian energy profile and may be collimated to form a more focused beam. A standard optical collimator may be used to collimate the laser light generated from a source, as would be understood by those skilled in the art.

At block 506, the Gaussian energy profile of the first beam of light is altered to form a second beam of light having a top hat profile. The energy profile may be altered using a beam shaping element, such as a fused silica diffractive optic.

At block 508, the second beam of light having the top hat profile is pulsed at a first beam spot towards the sheet of metal foil. The second beam of light may also be focused onto the first beam spot using one or more lenses, thus affecting the ablation depth and/or volume. The second beam of light may have femtosecond pulses 50 MHz, running at the rate of 50 m/sec, such that the pits or dimples have a linear pitch of 1 micron per line. If the length of the scan line is 200 mm, the vertical scan rate is 500 lines/sec. If the vertical pitch is 1 micron, then the web speed would be 500 microns/sec, or 30 mm/Min. 5.33 Min per sheet of 320 $cm^2$ area to mark the pattern.

At block 510, the second beam of light is pulsed at a second beam spot that is displaced from the first beam spot in a first direction. The first direction may be across a length of the metal foil stretched around the cylindrical body. The second beam of light is delivered from a laser head that may laterally move between a first position, where the second beam of light is pulsed at the first beam spot, and a second position where the second beam of light is pulsed at the second beam spot. It should be understood that this action may be repeated until dimples have been formed across an entire length of the metal foil.

At block 512, the sheet of metal foil is moved in a second direction around the cylindrical body. This second direction is substantially perpendicular to the first direction when viewed from the perspective of the laser head. The sheet of metal foil may move in the second direction after dimples have been formed across a length of the metal foil, in order to form more dimples across a new section of the metal foil.

Etching

Referring back to FIG. 2A-C, after laser marking the foil at step 206, the foil is etched at step 208, to increase the surface area of the foil. The foil is etched according to any method that increases the surface area, preferably electrochemical etching. Other methods include roughing the foil surface mechanically and chemical etching. Electrochemical etching increases the surface area of the foil by electrochemically removing portions of the foil to creates etch tunnels. Electrochemical etching is done according to any known etch process, such as the ones discussed in U.S. Pat. Nos. 4,474,657; 4,518,471; 4,525,249 and 5,715,133, which are incorporated herein by reference in their entirety.

The foil is etched in an electrolyte fluid that promotes electrochemical etching. The electrolyte comprises a halide and/or oxyhalide, preferably a chloride and/or oxychloride, and an oxidizer such as hydrogen peroxide, sodium perchlorate, sodium persulfate, cerium sulfate or sodium periodate. The pH of the electrolyte is maintained in the range of about 0.1 and 9.5, preferably between about 0.0 to about 8.0, and more preferably a pH of about 1.0 to about 3.0. An acid is added to the electrolyte to maintain the pH, for example hydrochloric acid. Alternative acids for use in the present invention include but are not limited to sulfuric, nitric, hydrobromic, and hydrofluoric acids; or organic acids such as formic, acetic, citric and para-toluenesulfonic acid. Other surface area enhancing etch solutions can be used with the present invention to produce similar results. Preferably, the electrolyte etch solution comprises about 1.3% by weight NaCl and about 3.5% by weight $NaClO_4$. The electrolyte is heated to a temperature of about 80° C. to about 100° C., with a preferred temperature of about 85° C. The foil is placed in the etch electrolyte and etched at a current density of about 0.1 to about 0.3 Amps/$cm^2$, preferably about 0.15 Amps/$cm^2$. The current density corresponds to an etch charge of about 5 to about 50 Coulombs/$cm^2$ for a specific amount of time, preferably about 36 Coulombs/$cm^2$ for about 4 minutes. The foil is etched to produce an enlargement of surface area of at least about 20 times.

Upon etching, the areas where the laser was applied etch more slowly or not at all. The hydrate layer and/or formed oxide layer adds more etch resist masking to methods using laser marking alone, e.g., the methods disclosed in U.S. Pat. No. 7,452,473, incorporated herein by reference in its entirety. The enhanced etch resist masking causes the fresh aluminum surface pits created by the femtosecond laser to be even higher energy density areas. The higher energy density areas promote the initiation and propagation of the etching dimples. The hydrate/formed oxide layer inhibit etching where present due to their electrical insulating and relative chemical inactivity properties in the etch solution. This passivates incidental high energy sites like rolling lines.

In certain embodiments, chemical treatment with sodium hydroxide is used to further expose the fresh aluminum surface pits.

At step 210 (FIGS. 2A-2C), after the foil is etched, the foil is widened in a chloride or nitrate containing electrolyte solution known to those skilled in the art, such as that disclosed in U.S. Pat. Nos. 3,779,877 and 4,525,249, which are incorporated herein by reference. The foil is then dipped into a deionized water bath at a temperature of 80° C. to 100° C., preferably 95° C., to form a hydrate on the foil surface.

A barrier oxide layer may be electrochemically formed onto the surface of the metal foil, sufficiently thick to support the intended use voltage, by placing the foil into a forming solution, including but not restricted to a solution based on azelaic acid, sebacic acid, suberic acid, adipic acid, dodecanedioic acid, citric acid or other related organic acids and salts. Preferably a citric acid is used solution at a temperature of about 80° C. to 100° C., preferably 85° C., at a current density of about 1 mA/cm$^2$ to 40 mA/cm$^2$, preferably 16 mA/cm$^2$. A formation voltage of about 50 to 800 Volts, preferably 445 V, can be applied to the foil to form the barrier oxide layer. The barrier oxide layer provides a high resistance to current passing between the electrolyte and the metal foils, also referred to as the leakage current. A high leakage current can result in poor performance and reliability of an electrolytic capacitor. In particular, a high leakage current results in a greater amount of charge leaking out of the capacitor once it has been charged.

A heat treatment of about 500° C.±20° C. may be applied to the foil following formation for about 1 to about 10 minutes, preferably about 4 minutes. The foil is then returned to the forming solution and allowed to soak with no applied potential for about 1 to about 10 minutes, preferably about 2 minutes. A second formation in the same electrolytic forming solution at high temperature is performed at a potential of about 435 Volts.

Next, the foils may be dipped in a suitable low concentration oxide-dissolving acid solution including but not restricted to phosphoric acid, formic acid, acetic acid, citric acid, oxalic acid, and acids of the halides. Preferably phosphoric acid is used at a concentration of about 1% to 10%, preferably a concentration of about 2%, at a temperature of about 60° C. to 90° C., preferably about 70° C., for a time of about one to about ten minutes, preferably about four minutes.

Finally, the foils are reformed at a voltage of about 435 Volts in a suitable forming solution, as discussed above, at a high temperature, preferably about 80° C. to about 100° C., more preferably about 85° C.

Electrolytic capacitors manufactured with anode foils etched according to the present invention may be utilized in ICDs, such as those described in U.S. Pat. No. 5,522,851 to Fayram, incorporated herein by reference. The increased capacitance per unit volume of the electrolytic capacitor will allow for a reduction in the size of the ICD.

While the invention has been particularly shown and described with reference to preferred embodiments thereof, it will be understood by those skilled in the art that various changes in form and details may be made therein without departing from the spirit and the scope of the invention.

What is claimed is:

1. A method of producing an electrode for a capacitor from a foil comprising:
   growing a hydrate layer on a surface of a foil;
   applying a laser beam to the hydrate layer so as to remove the hydrate layer from the foil,
      the laser beam being applied after the hydrate layer is grown on the foil; and
   etching the foil after the laser beam is applied to the portion of the foil, a second portion of the hydrate layer being present on the foil while etching the foil.

2. The method of claim 1, wherein the laser beam is applied so as to ablate the portion of the hydrate layer.

3. The method of claim 1, wherein the laser beam passes through the hydrate layer to the underlying foil so as to create a pattern on the surface of the foil.

4. The method of claim 3, wherein the laser beam is applied such that the laser beam forms dimples in the foil that penetrate the surface of the foil to a depth of approximately 0.1 micron to approximately 20 micron.

5. The method of claim 1, wherein etching the foil includes placing the foil in an electrochemical bath comprising a chloride electrolyte and heating said electrolyte to about 85° C.

6. The method of claim 5, wherein the foil is etched in the bath at a current density of about 0.10-0.25 Amp/cm$^2$.

7. The method of claim 1, wherein the laser beam is a femtosecond laser.

8. The method of claim 3, wherein the pattern is a hexagonal pattern.

9. The method of claim 1, wherein the laser beam is applied at a scan rate in the range of about 50 m/sec.

10. The method of claim 1, wherein the laser beam is applied with a spot size in a range of about 1 to about 10 microns.

11. The method of claim 1, further comprising:
   growing an oxide layer on a surface of the foil, and
   wherein the laser beam is applied so as to remove select portions of the hydrate layer and the oxide layer from the surface of the foil.

12. The method of claim 1, wherein the laser beam is applied while the hydrate layer is present on the surface of the foil.

13. The method of claim 1, wherein the hydrate layer is formed below the surface of the foil and the laser beam is applied so as to expose a portion of the foil located below the hydrate layer.

14. The method of claim 1, wherein a portion of the hydrate layer is present on the foil after the laser beam is applied.

15. The method of claim 1, wherein etching the foil is performed such that the hydrate layer acts as a mask during the etch.

16. A method of producing an electrode for a capacitor from a foil comprising:
   growing a hydrate layer on a surface of the foil;
   applying a laser beam to the hydrate layer so as to remove portions of the hydrate layer from the foil; and
   etching the foil after the laser beam is applied.

17. The method of claim 16, wherein the removed portions of the hydrate layer are arranged in a spot pattern with the spots each penetrating completely through the hydrate layer.

18. The method of claim 17, wherein the laser beam is applied such that the laser beam only partially penetrates through the foil to from a plurality of dimples on the foil surface.

19. The method of claim 18, wherein the laser beam is applied using a laser head having a scan rate of 50 m/sec and the dimples have a linear pitch of 1 micron per line.

20. The method of claim 16, wherein the laser beam is applied so as to mark the hydrate layer and/or oxide layer with spots arranged in a hexagonal array pattern.

21. The method of claim 16, wherein the laser beam is applied in a femtosecond time frame using a pulse repetition rate of approximately 50 MHz.

* * * * *